(12) United States Patent
Rubocki et al.

(10) Patent No.: US 7,442,505 B2
(45) Date of Patent: Oct. 28, 2008

(54) COMPOSITIONS AND METHODS FOR DETECTING HUMAN HERPESVIRUSES

(75) Inventors: Ronald Rubocki, Auburn, ME (US); Catherine Gebhart, Omaha, NE (US)

(73) Assignee: Board of Regents of the University of Nebraska, Omaha, NE (US)

( * ) Notice: Subject to any disclaimer, the term of this patent is extended or adjusted under 35 U.S.C. 154(b) by 0 days.

(21) Appl. No.: 11/026,299

(22) Filed: Dec. 30, 2004

(65) Prior Publication Data

US 2006/0147939 A1 Jul. 6, 2006

(51) Int. Cl.
*C12Q 1/68* (2006.01)
*C07H 21/02* (2006.01)

(52) U.S. Cl. .......................................... 435/6; 536/23.1

(58) Field of Classification Search ........................ None
See application file for complete search history.

(56) References Cited

OTHER PUBLICATIONS

Yamamoto et al. ("A single tube PCR assay for simultaneous amplification of HSV-1/2, VZV, CMV, HHV-6A/-6B, and EBV DNAs in cerebral fluid form patients with virus-related neurological diseases" Journal of NeuroVirology. 2000. 6: pp. 410-417).*
Tsurumi et al. ("A Single-Base Change within the DNA Polymerase Locus of Herpes Simplex Virus Type 2 Can Confer Resistance to Aphidicolin" Journal of Virology. Feb. 1987. pp. 388-394).*
Buck et al ("Design Strategies and Performance of Custom DNA Sequencing Primers" Biotechniques. 1999. 27(3): pp. 528-536).*
GENBANK Accession No. AY038367 (Oct. 2002).*
Tsurumi et al. ("A Single-Base Change within the DNA Polymerase Locus of Herpes Simplex Virus Type 2 Can Confer Resistance to Aphidicolin" Journal of Virology. Feb. 1987. pp. 388-394).*
Buck et al ("Design Strategies and Performance of Custom DNA Sequencing Primers" Biotechniques. 1999. 27(3): pp. 528-536).*
Stratagene ("Gene Characterization Kits" 1988).*
Casas et al. ("Detection of enteroviral RNA and specific DNA of herpesviruses by multiplex genome amplification" J Virol Methods. Jun. 1997;66(1):39-50).*
GENBANK Accession No. AF133604. Jul. 10, 2000.*
GENBANK Accession No. HS2POLD. Aug. 2, 1993.*
GENBANK Accession No. HH6DNAPOL. Aug. 23, 1995.*
Pozo et al. ("Detection and typing of lymphotropic herpesviruses by multiplex polymerase chain reaction" J Virol Methods. Apr. 1999;79(1):9-19).*
Elfath et al., "Multiplex PCR:Optimization and Application in Diagnostic Virology", Clinical Microbiology Reviews 2000 13(4) :559-570.
Markoulatos et al., "Detection and Typing of HSV-1, HSV-2, and VZV by a Multiplex Polymerase Chain Reaction", Journal of Clinical Laboratory Analysis 2000 14:214-219.
McElhinney et al., "Multiplex polymerase chain reaction for human herpesvirus-6, human cytomegalovirus, and human β-globin DNA", Journal of Virological Methods 1995 53:223-233.
Cassinotti et al., "Suitability and Clinical Application of a Multiplex Nested PCR Assay for the Diagnosis of Herpes Simplex Virus Infections", Journal of Medical Virology 1996 50:75-81.
Druce et al., "Utility of a Multiplex PCR Assay for Detecting Herpesvirus DNA in Clinical Samples", Journal of Clinical Microbiology 2002 40 (5) :1728-1732.
O'Neill et al., "Real-Time Nested Multiplex PCR for the Detection of Herpes Simplex Virus Types 1 and 2 and *Varicella zoster* Virus", Journal of Medical Virology 2003 71:557-560.
Read et al., "Laboratory Diagnosis of Common Viral Infections of the Central Nervous System by Using a Single Multiplex PCR Screening Assay", Journal of Clinical Microbiology 1999 37 (5) :1352-1355.
Yamamoto et al., "A single tube PCR assay for simultaneous amplification of HSV-1/-2, VZV, CMV, HHV-6A/-6B, and EBV DNAs in cerebrospinal fluid from patients with virus-related neurological diseases", Journal of NeuroVirology 2000 6:410-417.

* cited by examiner

*Primary Examiner*—Kenneth R. Horlick
*Assistant Examiner*—Christopher M. Babic
(74) *Attorney, Agent, or Firm*—Dann, Dorfman, Herrell & Skillman; Robert C. Netter, J.D.; Kathleen D. Rigaut, J.D

(57) ABSTRACT

The present invention relates to primer compositions and methods for identifying and distinguishing CMV, EBV-A/B, HSV-1/2, HHV-6 and VZV herpesviruses in a sample.

3 Claims, No Drawings

```
SEQUENCE LISTING

<160> NUMBER OF SEQ ID NOS: 21

<210> SEQ ID NO 1
<211> LENGTH: 200
<212> TYPE: DNA
<213> ORGANISM: Cytomegalovirus

<400> SEQUENCE: 1
gatcaagcat aagacgggac ggctgcctct catgttctat cgagagatta aacatttgtt      60
gagtcatgac atggtttggc cgtgtccttg gcgcgagacc ctggtgggtc gcgtggtggg     120
acctattcgt tttcacacct acgatcagac ggacgccgtg ctcttcttcg actcgcccga     180
aaacgtgtcg ccgcgctatc                                                 200

<210> SEQ ID NO 2
<211> LENGTH: 244
<212> TYPE: DNA
<213> ORGANISM: Herpes simplex virus

<400> SEQUENCE: 2
aacggccggg gtgtgttccg cgtgtgggac atcggccaga gccactttca gaagcgcagc      60
aagatcaagg tgaacgggat ggtgaacatc gacatgtacg gcatcatcac cgacaaggtc     120
```

-continued

```
aaactctcca gctacaagct gaacgccgtc gccgaggccg tcttgaagga caagaagaag    180
gatctgagct accgcgacat ccccgcctac tacgcctccg ggcccgcgca gcgcggggtg    240
atcg                                                                 244

<210> SEQ ID NO 3
<211> LENGTH: 301
<212> TYPE: DNA
<213> ORGANISM: Epstein-Barr virus

<400> SEQUENCE: 3
tttgggtctt agaatggtgg ccgggctgta aaattctgga ggacggagag ggcggccccg     60
gagttgttat caaagaggca ctggaggatg ttggccgctc cttggagcag cttgtcgaaa    120
taatgatcca cggccacggg aacgccgtgc cgctcggcgt aggccgggtc ctcggccatc    180
tccgtctttc tcgccccctt cactcccccc ttgggctcca caaagacgta ctggatgcgg    240
tcgtggatct ggggcagttc ctcgttgcgc tcgacgaact tctggtagac ggccaggtga    300
g                                                                    301

<210> SEQ ID NO 4
<211> LENGTH: 365
<212> TYPE: DNA
<213> ORGANISM: Varicella-zoster virus

<400> SEQUENCE: 4
attttgtgtt atcatagaac tgcgtaaaca ctcggcaagt aatacagata actcgctaca     60
ggaacgtatg ccacaagcgg tatccacctc ggctttgttt atataaaaat attgacagat    120
gccgtataca tgaactgcca cccttttttcc acatcgggac atgccaagta aagtaataac   180
ggtaccaagc ggtcgtgttg cagttgcaaa ccgggataca tctccattag acgcggcttc    240
tgttgtttcg acaatatcat atacatggaa tgtgttaaag cgggggtcaa acttatcccc    300
acgaaagtcg atttcccccc aaatattcac gcgtctaggc caggggctgg aacaacgaaa    360
atcca                                                                365

<210> SEQ ID NO 5
<211> LENGTH: 432
<212> TYPE: DNA
<213> ORGANISM: Herpesvirus 6

<400> SEQUENCE: 5
cgaaatactt ctccgcatgt ataggaatct tgtgttctaa cacatagttt ggatcttctg     60
ctaattcata gttatgcgtc tgtttattac cagtagatgg tgctattaac acatacataa    120
ttcggtcacc aacattcgga atttcttcct ttctctgcgc caaccttcta atgacgctaa    180
ggtgagccag attcggctgc ttatatgcag ccacctcctt ggaaagcaca gaagacaaca    240
tcaaatgtct cacgtctgcc cgattttgaa aaagctcctc ccgcgctttg cacagacgac    300
gcaaaatttt atgaataccc acaggcactc cttgctcacg caactgtgtt tgcgtcatgt    360
gagaaaactc cacagcagca gtctgaacct cttcatcaaa gaacaacaag tccacgatgt    420
ctttcaccac ac                                                        432

<210> SEQ ID NO 6
<211> LENGTH: 29
<212> TYPE: DNA
<213> ORGANISM: Artificial Sequence
<220> FEATURE:
```

```
<223> OTHER INFORMATION: Synthetic oligonucleotide primer

<400> SEQUENCE: 6
gtctgatcgt aggtgtgaaa acgaatagg                                29

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 7
aacatttgtt gagtcatgac atggtttg                                 28

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 8
gaagcgcagc aagatcaagg tgaac                                    25

<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 9
cggtagctca gatccttctt cttgtcc                                  27

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 10
ggcggccccg gagttgttat c                                        21

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 11
cagatccacg accgcatcca gta                                      23

<210> SEQ ID NO 12
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 12
actcgctaca ggaacgtatg ccacaagcgg                               30
```

<210> SEQ ID NO 13
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 13
gaaatcgact tcgtgggga taagtttgac c                                31

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 14
ggatcttctg ctaattcata gttatgcgtc                                 30

<210> SEQ ID NO 15
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 15
actgctgctg tggagttttc tcacatgac                                  29

<210> SEQ ID NO 16
<211> LENGTH: 500
<212> TYPE: DNA
<213> ORGANISM: Homo sapiens

<400> SEQUENCE: 16
tttcttttct taccagaagg ttttaatcca aataaggaga agatatgctt agaaccgagg    60
tagagttttc atccattctg tcctgtaagt attttgcata ttctggagac gcaggaagag   120
atccatctac atatcccaaa gctgaattat ggtagacaaa actcttccac ttttagtgca   180
tcaacttctt atttgtgtaa taagaaaatt gggaaaacga tcttcaatat gcttaccaag   240
ctgtgattcc aaatattacg taaatacact tgcaaaggag gatgttttta gtagcaattt   300
gtactgatgg tatggggcca agagatatat cttagaggga gggctgaggg tttgaagtcc   360
aactcctaag ccagtgccag aagagccaag gacaggtacg gctgtcatca cttagacctc   420
accctgtgga gccacaccct agggttggcc aatctactcc caggagcagg gagggcagga   480
gccagggctg ggcataaaag                                              500

<210> SEQ ID NO 17
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 17
agaaccgagg tagagttttc atccattctg                                 30

<210> SEQ ID NO 18
<211> LENGTH: 28
<212> TYPE: DNA
<213> ORGANISM: Artificial Sequence
<220> FEATURE:

```
<223> OTHER INFORMATION: Synthetic oligonucleotide primer

<400> SEQUENCE: 18
ggccaaccct agggtgtggc tccacagg                                          28

<210> SEQ ID NO 19
<211> LENGTH: 7
<212> TYPE: PRT
<213> ORGANISM: Herpes simplex virus

<400> SEQUENCE: 19

Lys Arg Ser Lys Ile Lys Val
1               5

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 20
gaagcgcagc aagatcaagg tsaac                                             25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (22)..(22)
<223> OTHER INFORMATION: "n" denotes inosine

<400> SEQUENCE: 21
gaagcgcagc aagatcaagg tnaac                                             25
```

COMPOSITIONS AND METHODS FOR DETECTING HUMAN HERPESVIRUSES

BACKGROUND OF THE INVENTION

There are more than 100 known herpesviruses in the family of Herpesviridae. Of these, eight are known to infect humans. The eight human herpesviruses are herpes simplex virus 1 (HSV-1); herpes simplex virus 2 (HSV-2); varicella-zoster virus (VZV); Epstein-Barr virus (EBV); cytomegalovirus (CMV); herpesvirus 6 (HHV-6); herpesvirus 7 (HHV-7); and herpesvirus 8 (HHV-8), also known as Kaposi's sarcoma associated herpesvirus (KSHV).

Based on the length of viral replication cycle and host tissue range, the herpesviruses are classified into three subfamilies, alpha-, beta-, and gamma-herpesviruses. Following primary infection, all herpesviruses establish latent persistent infections within tissues characteristic for each virus. For example, the alpha-herpesviruses HSV1, HSV2 and VZV are neurotropic, while EBV, CMV, HHV6, HHV7 and HHV8 are lymphotropic.

Human herpesvirus infections are very common and widely distributed. Serologic surveys indicate that >95% of adults worldwide have been infected by VZV, EBV, and HHV-6. Despite a vigorous anti-viral immune response, herpesviruses persist in the host following primary infection. This asymptomatic latent period may be interrupted by periods of viral reactivation during which virus replicates and clinical symptoms may occur. Examples include recurrent cold sores (HSV-1), herpes zoster (shingles) in older adults arising from VZV acquired during childhood (chicken pox), CMV pneumonitis in immunocompromised organ transplant patients, and recurrent mononucleosis in patients with chronic (EBV) mononucleosis syndrome.

In many cases, the diagnosis of herpesvirus infection cannot be accurately made by clinical findings alone. Symptoms are often nonspecific, e.g., fever, malaise, lymphadenopathy, and rash. Patients can sometimes be infected with more than one herpesvirus (e.g., frequent association of HHV-8 and EBV in primary effusion lymphoma, HSV-1 and HSV-2 in orogenital ulcers). Whereas infections with the CMV are usually amenable to acyclovir or gancyclovir anti-viral treatment, no suitable effective drug treatment is available for EBV, HHV-6, HHV-7, and HHV-8. Thus, identification of specific human herpesvirus infection is necessary before proper therapy can be selected.

The pathogenesis and clinical importance of the recently identified lymphotropic viruses HHV-6, HHV-7 and HHV-8 are not well understood. A better clinical understanding of these viruses requires the availability of appropriate diagnostic approaches for their detection and identification. All these factors, along with the worldwide impact of human herpesvirus infection, demonstrate the need for a reliable multiplex clinical assay for the detection and identification of human herpesviruses. Although a clinical assay need not differentiate EBV-1 from EBV-2 or HHV-6A from HHV-6B, it should be able to detect variants and to distinguish each type of herpesvirus from the other herpesviruses.

Current laboratory techniques for detection of herpesvirus infection include virus culture, viral serology, and viral DNA detection by molecular diagnostic methods such as PCR. Given the considerable limitations of culture and serology for herpesvirus detection, PCR detection methods have been developed. Molecular diagnostic methods such as PCR offer the distinct advantages of rapid turn-around time, high sensitivity, and high specificity for the detection of herpesvirus infections.

Several general approaches have been used to identify one or more types of human herpesvirus. Rozenberg and Lebon ((1991) *J. Clin. Microbiol.* 29(11):2412-7) describe a single-step PCR assay using a consensus primer pair for HSV-1, HSV-2, EBV, and CMV, followed by typing of the amplicons by restriction fragment length polymorphism analysis (RFLP). However, the complexity of RFLP restricts its use to sophisticated laboratory environments.

Tenorio, et al. ((1993) *J. Virol. Meth.* 44:261-9) disclose a nested amplification method for detecting herpesvirus. Non-degenerate oligonucleotides were used to generate a first set of amplicons which served as a substrate for a second, multiplex reaction for which primers were designed to produce different-size fragments for each related virus. However, because this method requires two separate, sequential PCR reactions, there is a significant risk of contamination of PCR reactions which leads to false positive reactions. Further, Elfath, et al. ((2000) *Clin. Microbiol. Rev.* 13:559-570) teaches that whenever possible, multiplex PCRs should avoid the use of nested primers requiring a second round of amplification and precautions should be taken to avoid false-negative results due to reaction failure.

Aono, et al. ((1994) *Acta Otolaryngol. Suppl.* 514:132-4) described a multiplex PCR using consensus primers for the detection of the three herpesviruses (HSV-1, HSV-2 and VZV) by virus-specific probe hybridization. Unlike restriction fragment length polymorphism, virus-specific probe hybridization is more compatible with clinical laboratory requirements of short cycle time and simplicity.

McElhinney, et al. ((1995) *J. Virol. Methods* 53:223-233) teach a three-target PCR method for the investigation of latent and active CMV and HHV-6 infection, and the use of human beta-globin DNA in the same reaction to avoid false-negative DNA amplifications for CMV.

van Devanter, et al. ((1996) *J. Clin. Microbiol.* 34(7):1666-71) developed a set of degenerate consensus primers for PCR amplification of conserved regions of the DNA polymerase gene. The resulting nested consensus primer PCR method allowed for amplification and identification of most (14 of 15) of the animal herpesviruses and 6 of 8 human herpesviruses (HHV-1, HHV-2, VZV, EBV, CMV, HHV-6B). The method did not amplify human DNA polymerase, or yeast/mold DNA polymerase that are common contaminants of human samples. However, the methodology exhibited a wide variation in sensitivity across the human herpesviruses tested. The LOD (limit of detection) varied between 1 copy per 100 ng DNA for HSV-1 and HSV-2, and 100 copies for EBV and VZV. No data was presented on amplification of HHV-7 or HHV-8. Each virus was identified by direct DNA sequencing of the amplified products obtained from an ethidium bromide-stained agarose gel. This method of DNA sequence typing is a highly complex, laborious method not appropriate for use in a clinical diagnostic laboratory. Moreover, this reference does not teach that the method can identify more than one herpesvirus in a single sample.

Colimon et al. ((1996) *J. Virol. Methods* 58:7-19) developed the use of "stair primers" to allow PCR amplification of viral genomes with frequent point mutations, such as HIV and hepatitis C virus. Minjolle, et al. ((1999) *J. Clin. Microbiol.* 37:950-3) adopted the use of these "stair primers" for herpesvirus assay, utilizing mixtures of consensus stair primers to amplify DNA polymerase for the detection of six of the eight human herpesviruses (HHV-1, HHV-2, VZV, EBV, CMV and HHV-6). However, amplicons were detected by virus-specific probe hybridization with chromogenic detection.

Ehlers, et al. ((1999) *Virus Genes* 18:211-220) developed an enhanced version of the van Devanter method. This reference noted that the van Devanter method exhibited a wide variation in binding of the degenerate primers to different herpesviruses and therefore deoxyinosine (dI) was substituted at degenerate positions within the van Devanter primers. DNA polymerase of some herpesviruses were not amplified at all by the dI-substituted primers (e.g., CMV). Using a mixture of dI-substituted and unsubstituted primers, it was found that the mixed primer set improved overall performance for herpesviruses from a range of species. Ehlers demonstrated that six of the eight human herpesviruses (HSV-1, HSV-2, VZV, EBV, CMV and HHV-8) could be amplified by this method, while reducing the virus-related variability in the limit of detection. However, the important issues of assay complexity and turn-around time were not addressed since Ehlers, like van Devanter, intended to utilize the assay primarily to support research rather than clinical analysis.

Pozo and Tenorio ((1999) *J. Virol. Methods* 79:9-19) developed a two-step consensus primer PCR assay for the six lymphotropic human herpesviruses. Six pairs of primers were used in a first PCR step to produce a virus-specific 194-bp amplicon of the DNA polymerase gene. Then six pairs of primers were used in a second PCR step in which the reverse primer targets a highly conserved region of each amplicon, and the forward primer governs a difference in amplicon size (e.g., 54-122 bp). Subsequent gel electrophoresis with ethidium bromide-staining allowed typing of each band by its migration rate on the gel. A limit of detection of 10-100 copies for the six lymphotropic herpesviruses was reported.

Johnson et al. ((2000) *J. Clin. Microbiol.* 38(9) :3274-9) developed a two-step PCR-based assay for detection and species identification of human herpesviruses. Two consensus primer pairs were used, one for the three α-herpesviruses, the other pair for the five β- and γ-herpesviruses. The primer pairs bracketing a highly conserved region of the DNA polymerase gene allowed amplification of all eight major human herpesviruses at a limit of detection of 10-100 copies, with the exception of CMV that had a limit of detection of 400 copies. Agarose gel electrophoresis was used for visual identification of fluorescent ethidium bromide-stained bands to identify sample amplicons positive for human herpesvirus. Positive amplicon reaction mixtures were then subjected to two separate restriction endonuclease digestions (BamHI and BstUI). The restriction digests were then subjected to agarose gel electrophoresis and the human herpesvirus species was identified based on the restriction fragment patterns (RFLP) on the two gels. However, the use of dual RFLP is complex and time-consuming for the clinical laboratory.

Yamamoto and Nakamura ((2000) *J. NeuroVirol.* 6:410-417) teach two sets of degenerate primers (P1 and P2, P3 and P4) specific for DNA polymerase from different herpesviruses. The resulting amiplicons (516, 514, 588, 510 and 522 bp corresponding to HSV-1/-2, VZV, CMV, HHV-6 and EBV, respectively) were separated on an ethidium bromide-stained gel and subsequently probed to confirm specificity of the PCR reaction.

Markoulatos et al. ((2000) *J. Clin. Lab. Anal.* 14:214-9) disclose a multiplex PCR assay for the detection of HSV-1, HSV-2 and VZV; however, this assay does not detect CMV, EBV or HHV-6. Subsequently, this assay was modified to also amplify CMV and EBV, however, the primer set did not amplify HHV-6 (Markoulatos, et al. (2003) *J. Clin. Lab. Anal.* 17:108-112). Additional multiplex assays have been disclosed; however, these references fail to teach detection of more than three types of herpesviruses (Cassinotti, et al. (1996) *J. Med. Virol.* 50(1):75-81; Read and Kurtz (1999) *J. Clin. Microbiol.* 37(5) :1352-5; O'Neill, et al. (2003) *J. Med. Virol.* 71(4) :557-60; Druce, et al. (2002) *J. Clin. Microbiol.* 40(5) :1728-32).

Robert, et al. ((2002) *J. Med. Virol.* 66:506-511) used a commercially available kit based on stair primers in a two stage multiplex PCR assay of six herpesviruses (HHV-1, HHV-2, VZV, EBV, CMV, and HHV-6) in tear fluid. Samples were amplified using the Argene HERPES CONSENSUS GENERIC™ Kit. Amplicons positive for herpesvirus were typed with the Argene HERPES IDENTIFICATION HYBRIDOWELL™ Kit by virus-specific probe hybridization with a chromogenic substrate for detection.

U.S. patent application Ser. No. 10/641,665 discloses assays for the detection and typing of ten human herpesviruses. The assays involve nested multiplex PCR using consensus primers to amplify conserved regions of the herpesvirus DNA. A dot blot/chemiluminescence assay and real-time PCR assay are disclosed as is a heteroduplex mobility assay.

Thus, the prior art is deficient in a one-step PCR-based assay capable of detecting and typing the major human herpesviruses in a clinical setting. The present invention fulfills this long-felt need.

SUMMARY OF THE INVENTION

The present invention relates to a composition for amplifying a DNA polymerase nucleic acid of a select human herpesvirus. The composition contains one or more primer sets of SEQ ID NO:6 and SEQ ID NO:7; SEQ ID NO:8 and SEQ ID NO:9; SEQ ID NO:10 and SEQ ID NO:11; SEQ ID NO:12 and SEQ ID NO:13; or SEQ ID NO:14 and SEQ ID NO:15; or degenerate oligonucleotides thereof. In a particular embodiment of the present invention, the composition further contains a primer set for amplifying a human beta-globin nucleic acid, wherein the primer set is represented by SEQ ID NO:17 and SEQ ID NO:18.

The present invention also relates to a method for identifying and distinguishing one or more types of select human herpesvirus in a sample. The method involves the steps of contacting a sample suspected of containing a human herpesvirus with one or more primer sets that specifically hybridize with a select human herpesvirus DNA Polymerase nucleic acid of SEQ ID NO:1, SEQ ID NO:2, SEQ ID NO:3, SEQ ID NO:4, or SEQ ID NO:5; amplifying the DNA polymerase nucleic acid of the select human herpesvirus, thereby generating an amplicon; and detecting the presence or absence of the amplicon, wherein the presence of the amplicon of a select human herpesvirus indicates the presence of the select human herpesvirus in the sample. One embodiment of this method is the inclusion of a primer set for amplifying a human beta-globin nucleic acid.

A kit for identifying and distinguishing one or more types of select human herpesvirus in a sample is also provided.

DETAILED DESCRIPTION OF THE INVENTION

The present invention relates to compositions and diagnostic assays for the simultaneous and unambiguous identification of one or more types of human herpesvirus in a clinical sample, even in the presence of mixed infection. The methods are based upon a one-step amplification using herpesvirus-specific primers to provide rapid detection of human herpesviruses from human tissues and body fluid. Specifically, a set of unique primers have been developed to hybridize with nucleic acids encoding DNA polymerase from each of CMV, HSV, EBV, VZV, and HHV-6 to generate five amplicons of distinct sizes in a multiplex amplification reaction. The method of the present invention is advantageously used over methods known in the art because it increases productivity by allowing laboratories to meet the increasing demand for testing without expansion of equipment, space or staff; decreases manipulations known to result in repetitive motion injuries; streamlines cumbersome molecular testing procedures thereby decreasing the potential for errors; and decreases direct expenses related to reagents, plastic ware, and technologist time.

Primers in accordance with the present invention are designed to specifically hybridize with a segment of the DNA polymerase coding sequence from the select herpesviruses CMV, HSV, EBV, VZV, or HHV-6, or the complementary strand thereof, and not hybridize with other DNA sequences under standard amplification conditions. In one embodiment, primer target sites are selected in a manner which avoids the creation of amplicons which overlap in size. Further, for completeness of amplification of DNA from samples and ease of analysis with current technologies, amplification of fragments in the range of 50 to 500 bp in size is desirable.

In one embodiment of the present invention, a herpesvirus DNA polymerase target sequence for primer hybridization and amplification of a herpesvirus-specific amplicon of 50 to 500 bp in size is a target sequence provided in Table 1.

TABLE 1

| Herpesvirus | GENBANK Accession No. | Target Location | SEQ ID NO: |
|---|---|---|---|
| CMV | AC146999 | 140460-140659 | 1 |
| HSV | AY038367 | 1483-1726 | 2 |
| EBV | AJ507799 | 153233-153533 | 3 |
| VZV | AB097933 | 49901-50265 | 4 |
| HHV-6 | AF157706 | 57813-58244 | 5 |

Exemplary primer hybridization sites in nucleic acids encoding DNA polymerase from various herpesviruses and the size of the resulting amplicons are listed in Table 2.

TABLE 2

| Herpesvirus Primer Name | GENBANK Accession No. | Target Location | Amplicon Size |
|---|---|---|---|
| CMV | | | |
| CMV 100-F | AC146999 | 140581-140609 | 100 bp |
| CMV 100-R | | 140510-140537 | |
| HSV | | | |
| HSV 144-F | AY038367 | 1533-1557 | 144 bp |
| HSV 144-R | | 1650-1676 | |
| EBV | | | |
| EBV 201-F | AJ507799 | 153283-153303 | 201 bp |
| EBV 201-R | | 153461-153483 | |
| VZV | | | |
| VZV 265-F | AB097933 | 49951-49980 | 265 bp |
| VZV 265-R | | 50185-50215 | |
| HHV-6 | | | |
| HHV-6 332-F | AF157706 | 57863-57892 | 332 bp |
| HHV-6 332-R | | 58166-58194 | |

The use of the primer hybridization sites exemplified herein have been shown to provide accurate identification of each herpesvirus as the primer sets for each herpesvirus have been selected so that the amplicons generated do not overlap in length.

Accordingly, the present invention encompasses a composition containing one or more of the herpesvirus primer sets listed in Table 3 for amplifying DNA polymerase nucleic acids from one or more select herpesviruses.

TABLE 3

| Primer | Sequence (5' -> 3') | SEQ ID NO: |
|---|---|---|
| CMV 100-F | GTC TGA TCG TAG GTG TGA AAA CGA ATA GG | 6 |
| CMV 100-R | AAC ATT TGT TGA GTC ATG ACA TGG TTT G | 7 |
| HSV 144-F | GAA GCG CAG CAA GAT CAA GGT GAA C | 8 |
| HSV 144-R | CGG TAG CTC AGA TCC TTC TTC TTG TCC | 9 |
| EBV 201-F | GGC GGC CCC GGA GTT GTT ATC | 10 |
| EBV 201-R | CAG ATC CAC GAC CGC ATC CAG TA | 11 |
| VZV 265-F | ACT CGC TAC AGG AAC GTA TGC CAC AAG CGG | 12 |
| VZV 265-R | GAA ATC GAC TTT CGT GGG GAT AAG TTT GAC C | 13 |
| HHV-6 332-F | GGA TCT TCT GCT AAT TCA TAG TTA TGC GTC | 14 |
| HHV-6 332-R | ACT GCT GCT GTG GAG TTT TCT CAC ATG AC | 15 |

The primers are named according to the herpesvirus which they amplify, and are designated "F" or "R" for "forward" and "reverse", respectively.
Nucleotide bases are designated as adenine (A), thymine (T), guanine (G), and cytosine (C).

Advantageously, primers represented by SEQ ID NO:8 and SEQ ID NO:9 amplify the DNA polymerase gene from HSV-1 and HSV-2 and primers represented by SEQ ID NO:10 and SEQ ID NO:11 amplify the DNA polymerase gene from EBV-A and EBV-B. The composition of the present invention can contain one, two, three, four, or all five sets of primers and in one embodiment, further contains a primer set for amplifying a segment of a nucleic acid encoding human beta-globin. A suitable target sequence for primer hybridization and amplification of a human beta-globin amplicon of 50 to 500 bp in size is nucleotide positions 70021-70520 (SEQ ID NO:16) of GENBANK Accession number NG_000007. An exemplary human beta-globin primer set is provided as SEQ ID NO:17 (5'-AGA ACC GAG GTA GAG TTT TCA TCC ATT CTG-3') and SEQ ID NO:18 (5'-GGC CAA CCC TAG GGT GTG GCT CCA CAG G-3'), which are designed to hybridize to nucleotide positions 70071-70100 and 70443-70470, respectively, of GENBANK Accession number NG_000007. The beta-globin primers designated β-glob 400-F (SEQ ID NO:17) and β-glob 400-R (SEQ ID NO:18) generate a 400 bp amplicon. Advantageously, the inclusion of such primers can demonstrate the presence or absence of amplifiable DNA in a sample and detect the presence of an inhibitor.

It is contemplated that the primer sets disclosed herein can be used in combination with other primer sets specific for other target sequences. One of skill in the art can readily combine these primer sets by, e.g., adjustment of amplification conditions and primer concentrations to identify an equilibrium in which all target nucleic acids can be amplified. For example, a primer set to amplify nucleic acids from HHV-7 or HHV-8 can be readily added to a multiplex amplification reaction disclosed herein, so long as amplification of these additional nucleic acids results in the generation of amplicons which either do not overlap in size, or can be labeled in some way to make amplicons which do overlap in size distinguishable from one another.

Similarly, modifications can be made to the primers utilized in the present invention which change the exact sequence of a primer but still allow the primer to function as stipulated in the present invention during amplification. For example, modifications can be made within the primer sequence or at the 5' or the 3' ends of the primers to incorporate additional target sequence or for tagging purposes.

As DNA polymerase nucleic acids are used as targets for the primers disclosed herein, these sequences are expected to have a low rate of mutation and therefore should not vary. However, mutations which do not alter the protein sequence of the DNA polymerase (i.e., mutations which alter codon usage) may occur and therefore primers of the present invention are also intended to include degenerate primers which compensate for changes in the codon usage at the selected target sites for the primers of SEQ ID NOs:6-15, 17 and 18. Such alternate codons are well-established in the art and are listed in Table 4.

TABLE 4

| First Position (5' end) | Second Position | | | | Third Position (3' end) |
|---|---|---|---|---|---|
| | U | C | A | G | |
| U | Phe | Ser | Tyr | Cys | U |
| | Phe | Ser | Tyr | Cys | C |
| | Leu | Ser | Stop | Stop | A |
| | Leu | Ser | Stop | Trp | G |
| C | Leu | Pro | His | Arg | U |
| | Leu | Pro | His | Arg | C |

TABLE 4-continued

| First Position (5' end) | Second Position | | | | Third Position (3' end) |
|---|---|---|---|---|---|
| | U | C | A | G | |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

By way of illustration, primer HSV 144-F, 5'-GAA GCG CAG CAA GAT CAA GGT GAA C-3' (SEQ ID NO:8) codes for amino acid residues Lys-Arg-Ser-Lys-Ile-Lys-Val (SEQ ID NO:19). A GTG->GTC mutation would still code for a valine, however, primer hybridization to such an HSV mutant may change. Thus, suitable degenerate primer such as 5'-GAA GCG CAG CAA GAT CAA GGT (G/C)AA C-3' (SEQ ID NO:20) or 5'-GAA GCG CAG CAA GAT CAA GGT IAA C-3' (SEQ ID NO:21) can be designed which take into account both alternate codons. In addition to the use of inosine (I) which can bind to G or C, degenerate primers can be produced using other universal bases including, but not limited to, nitroindoles such as 5-nitroindole or 3-nitropyrrole (Loakes, et al. (1995) *Nucleos. Nucleot.* 14:1001-1003), degenerate nucleotides dP or dK, an acyclic nucleoside analog containing 5-nitroindazole (Van Aerschot, et al. (1995) *Nucleos. Nucleot.* 14:1053-1056) or a purine analog 1-(2-deoxy-β-D-ribofuranosyl)-imidazole-4-carboxamide (Sala, et al. (1996) *Nucl. Acids Res.* 24:3302-3306).

Modifications to the 5' end of a primer can be made, for example, in order to adjust the $T_m$ of hybridization or to add tags (e.g., fluorescent labels). Changes to the 3' end of a primer can be made, for example, in order to reduce the generation of non-specific, artifactual amplicons (the addition or deletion of one or two bases can make a dramatic difference in terms of hybridization specificity). Those of skill in the art will recognize that changes in the sequences of the primers employed in the practice of the present invention can be made without impairing the utility of the primer in the practice of the present invention. All such changes are intended to be encompassed by the compositions and methods of the present invention. Any primers whose sequences are based on the primers disclosed in the present invention (i.e., which have greater than about 75% homology to the primers utilized in the present invention) and which can function as equivalents of the primers actually utilized in the Examples of the present invention (i.e., can be used in an amplification of herpesvirus DNA polymerase nucleic acids resulting in the generation of amplicons from multiple co-amplified herpesviruses which do not overlap in size) are intended to be encompassed by the present invention.

Additionally, the primers used in the present invention can be modified by the insertion of non-template related nucleotides to satisfy certain PCR requirements, such as compatible melting temperatures, to minimize primer dimer formation, or to minimize non-target primer binding.

Further, those of skill in the art will recognize that other primers with totally different sequences than those employed in the Examples of the present invention can be employed to effect the multiplex amplification of the present invention.

Any primer set which hybridizes to a herpesvirus DNA polymerase target sequence disclosed herein (i.e., SEQ ID NO:1-5) can be used in the practice of the present invention. In general, suitable primer sets will not form primer dimers; will amplify only one type of herpesvirus; will produce amplicons ranging in size from 50 to 500 bp; and will generate amplicons which either do not overlap in size, or can be labeled in some way to make the amplicons which do overlap in size distinguishable from one another. Further, it is particularly desired that the primers of the primer set are of a length which enhances the specificity of the primers for a select herpesvirus (e.g., at least 20 bp in length) . Moreover, primer sets of the present invention should not require amplification conditions or protocols which are incompatible with multiplex amplification (Edwards, et al. (1994) *PCR Meth. Applic.* 3:565-575), e.g., a $T_m$ which is significantly different from the other multiplex primers. By way of example, the primer sets exemplified herein have similar melting temperatures ($T_m$) (Table 5) which facilitates multiplex amplification of the herpesvirus-specific amplicons.

TABLE 5

| Primer | $T_m^A$ | $T_m^B$ |
|---|---|---|
| CMV 100-F | 60.4 | 84 |
| CMV 100-R | 59.1 | 76 |
| HSV 144-F | 62.1 | 76 |
| HSV 144-R | 60.7 | 82 |
| EBV 201-F | 63.2 | 70 |
| EBV 201-R | 60.7 | 72 |
| VZV 265-F | 70.1 | 94 |
| VZV 265-R | 65.8 | 90 |
| HHV-6 332-F | 59.1 | 84 |
| HHV-6 332-R | 63.6 | 86 |
| β-globin 400-F | 62.2 | 86 |
| β-globin 400-R | 72.2 | 94 |

$^A T_m$ determined using the calculator at http://www/gensetoligos.com/calculation/calculation.html.
$^B T_m$ determined using the formula $2(A + T) + 4(C + G)$.

Synthesis of the primers used in the present invention can be conducted using any standard procedure for oligonucleotide synthesis. Many such procedures are well-known to those skilled in the art and are suitable for use in the practice of the present invention.

The herpesvirus DNA polymerase target sequences and primers disclosed herein find application in identifying and distinguishing one or more types of select human herpesvirus in a sample. Such a method is carried out by contacting a sample suspected of containing a human herpesvirus with a one or more of the primer sets that specifically hybridize with a select human herpesvirus DNA Polymerase nucleic acid of SEQ ID NO:1, SEQ ID NO:2, SEQ ID NO:3, SEQ ID NO:4, or SEQ ID NO:5; amplifying the DNA polymerase nucleic acid of a select human herpesvirus, thereby generating an amplicon; and detecting the presence or absence of the amplicon, wherein the presence of the amplicon of a select human herpesvirus indicates the presence of the select human herpesvirus in the sample.

In the context of this invention, a sample is any fluid, cell, or tissue, living or dead, or a nucleic acid derived therefrom. Those of skill in the art will recognize that the samples to be analyzed by the method of the present invention can come from any of a wide variety of sources suspected of containing a human herpesvirus, including but not limited to, environmental samples (e.g., food) and biological samples (e.g., blood, semen, vaginal cells, saliva, buccal cells, donated organs, and the like). The sample can be obtained by a variety of means such as by biopsy, swabbing, and the like. The sample can be obtained by a physician or healthcare professional in a hospital or other healthcare environment. Samples suspected of containing a human herpesvirus include those being tested for quality control (e.g., donated blood or organs) or samples isolated from individuals exhibiting symptoms consistent with one or more herpesvirus infections.

When the sample is a nucleic acid derived from a fluid, cell, or tissue, the sample can be prepared using any standard method which is compatible with amplification. Many suitable methods are known to those of skill in the art and include, but are not limited to, nucleic acid sample preparation as described by Pate, et al. ((1984) *Somat. Cell Mol. Genet.* 10:483-493) and Gill, et al. ((1985) *Nature* 318:577-579) and commercially available kits such as those provided by QIAGEN®.

Optionally, nucleic acid concentrations can be measured prior to use in the method of the present invention using any standard method of nucleic acid detection. For example, DNA concentration can be measured fluorometrically using a technique such as that described by Brunk et al. ((1979) *Anal. Biochem.* 92:497-500).

Once a sample, or nucleic acid thereof, is isolated, one or more herpesvirus target nucleic acids are amplified. A herpesvirus primer set can be used alone or in a multiplex reaction (i.e., combinations of two, three, four, or five primer sets) for the purpose of co-amplification in a single vessel and co-analysis (e.g., separated by electrophoresis in a single electrophoretic well). Alternatively, amplicons can be amplified independently in separate vessels and subsequently combined for analysis. In one embodiment, a multiplex amplification is carried out with at least two herpesvirus primer sets (e.g., those disclosed herein as SEQ ID NO:6-15) . In other embodiments, a multiplex amplification is carried out with at least three, four, or five herpesvirus primer sets (e.g., those disclosed herein as SEQ ID NO:6-15). Further, in any one of these embodiments, a human beta-globin primer set (e.g., those disclosed herein as SEQ ID NO: 17-18) can be used as an internal control.

Many different amplification methods are well-known to those of skill in the art and can be used in accordance with the method of the present invention. Such methods include, but are not limited to, PCR (Saiki, et al. (1988) *Science* 239:487-491), ligase chain reaction (LCR) and strand-displacement amplification (SDA). In one embodiment of the present invention, the sample is subjected to a standard PCR amplification using, e.g., the primer sets and thermocycling conditions exemplified herein which have been worked out to simultaneously amplify nucleic acids from CMV, HSV, EBV, VZV, or HHV-6 using the same protocol (i.e., same temperatures for each step of denaturation, annealing and elongation) so that the amplification will result in the production of a sufficient concentration of amplicons for each herpesvirus. While a hybridization (i.e., annealing) temperature of approximately 65° C. was used in the amplification reaction exemplified herein, it will be appreciated by one of skill in the art that other suitable amplification temperatures (e.g., ranging from 45° C. to 72° C.) and conditions (e.g., addition of detergents or other reagents) can be used to optimize primer hybridization thereby increasing specificity. Such adjustments in amplification temperatures and conditions are well-known and routine in the art.

Once one or more herpesvirus amplicons have been produced from the multiplex amplification step of the present method, the amplicons are detected. The step of detecting the amplicons can be carried out by a variety of methods including, but not limited to, size-separation and analysis using well-established methods such as polyacrylamide gel electrophoresis or capillary electrophoresis or mass spectrometry.

In one embodiment of the present invention, the amplicons of the multiplex amplification reaction are separated by electrophoresis. Gel preparation and electrophoresis procedures and conditions are well-established in the art, and can be carried out by either slab gel or capillary electrophoresis systems. Identification of the separated amplicons then occurs based on amplicon size. Desirably, the electrophoresis of all herpesvirus amplicons, and optionally the beta-globin control amplicon, is carried out in a single electrophoretic well. However, one of skill in the art will recognize that analysis of the amplicons can be carried out by electrophoresis in a plurality of channels, if desired. Once the amplicons are separated in a slab gel or capillary electrophoresis system, the amplicons and any other DNA (e.g., DNA markers) can then be visualized and analyzed. Visualization can be accomplished using any one of a number of techniques well-known to those of skill in the art including, but not limited to, silver staining, using reporters such as radioisotopes, fluorophores, chemiluminescent agents and enzymes in combination with detectable substrates, and the like. The amplicons produced by the amplification step are analyzed by comparing amplicon size with molecular weight markers which provide a sensitive and accurate determination of the molecular weight of the amplicons. Molecular weight markers can be obtained from commercial sources or can be generated from a combination of the herpesvirus amplicons (i.e., a positive control).

Alternatively, fluorescently-labeled (Ziegle, et al. (1992) Genomics 14(4):1026-31) primers can be used for each herpesvirus in the multiplex amplification reaction followed by detection of the labeled products using a fluorometric detector. With automated fluorescent imaging, rapid detection and analysis of multiplex amplification products can be achieved. For fluorescent analyses, one fluoresceinated primer can be included in the amplification reaction of each target nucleic acid. Separation of the amplicons produced using labeled primers can then be achieved by electrophoresis, and the labeled amplicons from each herpesvirus can be detected by its fluorescent emission upon excitation by photons of the appropriate wavelength post-electrophoresis. When separated by gel electrophoresis, the gel can be analyzed by, for example, a FLUORIMAGER™ analyzer (Molecular Dynamics, Sunnyvale, Calif.) or FMBIO™ (Hitachi Corp., San Bruno, Calif.), which scan the gel, locate and measure the distance of migration of the amplicon.

Alternatively, measurements can be made in real-time during an electrophoresis run as each labeled amplicon is excited by a laser beam during migration near the end of its channel, and its running time is recorded, for example with the ALF, ALFEXPRESS™, VGI MICROGENE CLIPPER™, or ABI PRISM™ analyzer. Under denaturing conditions, fragment length is proportional to run time, and can be calculated from the sample and calibration standard run times and known calibration fragment lengths.

In another embodiment, amplicons are detected by mass spectrometry. Mass spectrometry is advantageously used because it is intrinsically a parallel detection scheme without the need for radioactive or fluorescent labels, since every amplicon is identified by its molecular mass. The current state of the art in mass spectrometry is such that less than femtomole quantities of material can be readily analyzed to afford information about the molecular contents of the sample. An accurate assessment of the molecular mass of the material can be quickly obtained, even with small differences in molecular mass. Intact molecular ions can be generated from amplicons using one of a variety of ionization techniques to convert the sample to gas phase. These ionization methods include, but are not limited to, electrospray ionization (ES), matrix-assisted laser desorption ionization (MALDI) and fast atom bombardment (FAB). For example, MALDI of nucleic acids, along with examples of matrices for use in MALDI of nucleic acids, are described in WO 98/54751.

Mass detectors which can be employed include, but are not limited to, Fourier transform ion cyclotron resonance mass spectrometry (FT-ICR-MS), ion trap, quadrupole, magnetic sector, time of flight (TOF), Q-TOF, and triple quadrupole.

The detection of a particular amplicon amplified from a sample is indicative of the presence of the corresponding select herpesvirus in the sample. For example, when using the primers exemplified herein, the presence of a 100 bp amplicon is indicative of the presence of CMV in the sample. Likewise, the presence of a 144, 201, 276 or 332 bp amplicon is indicative of the presence of HSV-1/2, EBV-A/B, VZV, or HHV-6, respectively. Therefore, the method of the present invention can be used to definitively identify and distinguish which type(s) of herpesviruses are present in a sample to, e.g., select the best course of treatment or assess the risk of transmitting a disease in donated blood or organs. Such examination prevents transfer of viruses from a donor to a recipient via a transplanted organ.

The present invention also relates to kits encompassing the primer sets and methods disclosed herein. A basic kit is composed of a container having one or more herpesvirus primer sets (e.g., SEQ ID NO:6 and SEQ ID NO:7; SEQ ID NO:8 and SEQ ID NO:9; SEQ ID NO:10 and SEQ ID NO:11; SEQ ID NO:12 and SEQ ID NO:13; or SEQ ID NO:14 and SEQ ID NO:15) for the amplification of nucleic acids encoding DNA polymerase from one or more herpesvirus (e.g., CMV, HSV, VZV, or HHV-6). A primer set for human beta-globin amplification (e.g., the primer set of SEQ ID NO:17 and SEQ ID NO:18) or another "house-keeping" gene and instructions for use of the kit can optionally be included.

Other optional kit components include molecular weight markers, a sufficient quantity of enzyme for amplification, amplification buffer, loading solution for preparation of the amplified material for gel electrophoresis, human genomic DNA as a template control, and a protocol and manual to educate the user. The amounts of the various reagents in the kits also can be varied depending upon a number of factors, such as the optimum sensitivity of the process. It is within the scope of the present invention to provide test kits for use in manual applications or test kits for use with automated detectors or analyzers.

The invention is described in greater detail by the following non-limiting examples.

EXAMPLE 1

PCR Amplification of Herpesvirus DNA

PCR reagents including 10× PCR buffer, $MgCl_2$, dNTP stock, and PLATINUM® Taq DNA polymerase were obtained from INVITROGEN™ (Carlsbad, Calif.) and routinely stored at −20° C. Primers listed in Table 2 were obtained from various sources, diluted to a 400 μM stock using 1× Tris-EDTA buffer and routinely stored at −70° C. For use in PCR reactions, the primers were diluted to a 20 μM stock with sterile water and aliquoted in volumes usable for making a PCR master mix. The PCR master mix components and their respective volumes used for obtaining a total reaction volume of 25 μL are listed in Table 6.

TABLE 6

| Reagent | Volume (μL) |
| --- | --- |
| 10× PCR Buffer | 2.5 |
| 50 mM MgCl$_2$ | 2.0 |
| 2 mM dNTP stock | 2.5 |
| 20 μM primer CMV 100-F | 0.5 |
| 20 μM primer CMV 100-R | 0.5 |
| 20 μM primer EBV 201-F | 0.5 |
| 20 μM primer EBV 201-R | 0.5 |
| 20 μM primer HHV-6 332-F | 0.5 |
| 20 μM primer HHV-6 332-R | 0.5 |
| 20 μM primer HSV 144-F | 0.5 |
| 20 μM primer HSV 144-R | 0.5 |
| 20 μM primer VZV 265-F | 0.5 |
| 20 μM primer VZV 265-R | 0.5 |
| 20 μM primer β-globin 400-F | 0.05 |
| 20 μM primer β-globin 400-R | 0.05 |
| Sterile Water | 1.65 |
| PLATINUM ® Taq Polymerase | 0.25 |

The reagents listed in Table 6 were combined in a master mix, aliquoted and stored at −20° C.

A positive control was developed by pooling blood samples known to contain EBV, CMV and HHV-6 and cell cultures having HSV-1 and VZV. Beta-globin was contributed by the blood samples. The positive control consisted of 35 μL of a blood sample containing CMV, 85 μL of a blood sample containing EBV, 5 μL of a blood sample containing HHV-6, 20 μL of culture containing HSV, and 5 μL of culture containing VZV. The positive control was aliquoted into multiple tubes (~33 μL per tube). For use in PCR amplification, the aliquoted control was thawed and 22 μL of sterile water was added to each aliquote and thoroughly mixed.

For each PCR reaction multiple precautions were taken to ensure high quality reactions including, treating setup bench top with bleach before setting up the PCR reaction; wearing clean gloves when labeling and setting up the PCR reaction; separating patient reaction tubes by at least one space; separating control DNA reaction tubes from patient reaction tubes by at least one space; using fresh aliquoted sterile water; using designated DNA pipettes for all patient's DNA samples and control DNA; opening only one tube at a time; and aliquoting the master mix/PLATINUM® Taq Polymerase to tubes first and then adding patient and positive control to the tube.

PCR amplification was conducted in a total reaction volume of 25 μL, wherein 10 μL of sample DNA or sample DNA/water was added to 15 μL of master mix/PLATINUM® Taq Polymerase. When analyzing DNA extracted from body fluids, CSF or swabs, 10 μL of DNA was used. When analyzing DNA extracted from blood, bone marrow, peripheral stem cells, urine, or paraffin, 5 μL of DNA and 5 μL of water were used. When the DNA was organically extracted, it was quantitated and 0.5 μg was used in the PCR amplification assay. For the positive control, 5 μL of DNA and 5 μL water were used. Reaction tubes were vortexed and centrifuged prior to amplification. Using a GENEAMP® 9700 Thermalcycler (Applied Biosystems, Foster City, Calif.), the herpesvirus DNA polymerase amplicons were amplified under the following amplification protocol: 1 cycle at 94° C. for 4 minutes; 45 cycles of 94° C. for 30 seconds, 66° C. for 30 seconds, and 72° C. for 30 seconds; and 72° C. for 4 minutes. At the end of the amplification protocol, the samples were held at 15° C. until analyzed.

The resulting herpesvirus DNA polymerase amplicons were size-separated for analysis. Molecular weight markers (100 bp ladder; 12 μL), sample PCR reactions (10 μL mixed with ~2 μL loading dye) and control reactions (10 μL mixed with ~2 μL loading dye) were loaded onto a 3% agarose gel and electrophoresed until the dye front moved off the gel. The positive control was found to contain a 100 bp CMV band, a 144 bp HSV-1/2 band, a 201 bp EBV-A/B band, a 265 bp VZV band, a 332 HHV-6 band, and a 400 bp β-globin band. The patient samples either had no band present (i.e., no detectable herpesvirus infection) or had one or more bands corresponding to the various herpesviruses assayed for.

What is claimed is:

1. A composition for amplifying a DNA polymerase nucleic acid of a select human herpesvirus comprising three or more primer sets of:
   SEQ ID NO:6 and SEQ ID NO:7; specific for amplification of CMV;
   SEQ ID NO:8 and SEQ ID NO:9; specific for amplification of HSV;
   SEQ ID NO:10 and SEQ ID NO:11; specific for amplification of EBV;
   SEQ ID NO:12 and SEQ ID NO:13; specific for amplification of VZV or
   SEQ ID NO:14 and SEQ ID NO:15; specific for amplification of HHV, each of said primers generating amplicons of five distinct sizes which are indicative of the type of herpesvirus being amplified.

2. A kit for identifying and distinguishing one or more types of select human herpesvirus in a sample comprising a composition of claim 1.

3. A method for identifying and distinguishing one or more types of select human herpesvirus in a sample comprising:
   a) contacting a DNA containing sample with the composition of claim 1;
   b) subjecting said sample to conditions effective for polymerase chain reaction such that amplicons are formed if said select human herpesvirus is/are present; and
   c) detecting the presence and size of said amplicon if any, thereby identifying and distinguishing said herpesvirus present in said sample.

* * * * *